US012728112B2

(12) United States Patent
Li et al.

(10) Patent No.: US 12,728,112 B2
(45) Date of Patent: Sep. 8, 2026

(54) APPLICATION OF SESQUITERPENE LACTONE IN PREPARING DRUG FOR TREATING OPTIC NEURITIS

(71) Applicant: ACCENDATECH LUOYANG CO., LTD., Luoyang (CN)

(72) Inventors: Hongen Li, Henan (CN); Jianmiao Gong, Luoyang (CN); Shiqi Bao, Luoyang (CN); Xuemei Zhang, Luoyang (CN)

(73) Assignee: ACCENDATECH LUOYANG CO., LTD., Luoyang (CN)

( * ) Notice: Subject to any disclaimer, the term of this patent is extended or adjusted under 35 U.S.C. 154(b) by 750 days.

(21) Appl. No.: 18/043,376

(22) PCT Filed: Aug. 28, 2020

(86) PCT No.: PCT/CN2020/112117

§ 371 (c)(1),
(2) Date: Feb. 28, 2023

(87) PCT Pub. No.: WO2022/041123

PCT Pub. Date: Mar. 3, 2022

(65) Prior Publication Data

US 2023/0346742 A1 Nov. 2, 2023

(51) Int. Cl.

*A61P 25/00* (2006.01)
*A61K 31/365* (2006.01)
*A61P 27/02* (2006.01)
*A61P 37/06* (2006.01)

(52) U.S. Cl.

CPC ............ *A61K 31/365* (2013.01); *A61P 25/00* (2018.01); *A61P 27/02* (2018.01); *A61P 37/06* (2018.01)

(58) Field of Classification Search

CPC ......... A61K 31/365; A61P 27/02; A61P 37/06
See application file for complete search history.

(56) References Cited

U.S. PATENT DOCUMENTS

2019/0314324 A1 10/2019 Lin et al.

FOREIGN PATENT DOCUMENTS

| | | | | | |
|---|---|---|---|---|---|
| CN | 111494366 A | * | 1/2019 | ........... | A61K 31/365 |
| CN | 109897022 A | | 6/2019 | | |
| CN | 111743894 A | | 10/2020 | | |
| EP | 3320901 A1 | | 5/2018 | | |

OTHER PUBLICATIONS

Qin, Xiangyang et al.; "Micheliolide inhibits LPS-induced inflammatory response and protects mice from LPS challenge."; Scientific Reports; vol. 6, srep 23240; Mar. 17, 2016; pp. 1-13.
Li, Qiuying et al.; "ACT001 modulates the NF-κB/MnSOD/ROS axis by targeting IKKβ to inhibit glioblastoma cell growth."; Journal of Molecular Medicine; vol. 98; Jan. 4, 2020; pp. 263-277.
Levin, Marc H. et al.; "Optic neuritis in neuromyelitis optica.", Progress in Retinal and Eye Research.; vol. 36; Mar. 30, 2013; pp. 159-171.

* cited by examiner

*Primary Examiner* — Erich A Leeser
(74) *Attorney, Agent, or Firm* — NKL Law; Allen Xue

(57) ABSTRACT

A sesquiterpene lactone compound is used in preparing a drug for treating optic neuritis. The sesquiterpene lactone compound and a pharmaceutically acceptable auxiliary material are prepared into a drug. ACT001 can effectively inhibit the inflammatory response of microglia, and can significantly reduce the release of inflammatory factors, comprising NO, TNF-α, and IL-6. It has the effect of inhibiting the proliferation of BV2 cells and curative effects on optic neuritis, particularly neuromyelitis optica.

5 Claims, 3 Drawing Sheets

APPLICATION OF SESQUITERPENE LACTONE IN PREPARING DRUG FOR TREATING OPTIC NEURITIS

TECHNICAL FIELD

The present disclosure belongs to the field of pharmaceuticals for autoimmune diseases, and particularly relates to use of a sesquiterpene lactone compound for manufacturing a drug for treating optic neuritis.

BACKGROUND

Neuromyelitis optica (NMO) is a demyelinating disease that involves the optic nerve and spinal cord. The earliest report of the disease was in 1872, and it was originally thought to be a single-course central nervous system disease. In Asian countries, there are many reports on NMO, and in our country only, there are over 300,000 NMO patients at present. In the outpatient service of neuroophthalmology, classical NMO-related optic neuritis (C-NMO-ON) is mainly characterized by simultaneous or sequential onset in two eyes, rapid diminution of vision, with or without ocular pain; visual function recovery is poor, often leaving both eyes or at least one eye in severe visual impairment. Recurrent NMO-related optic neuritis (R-NMO-ON) mostly occurs in a single eye and is easy to relapse. Visual function damage can be partially recovered, but the recovery is gradually weakened along with the increase in the frequency of occurrence. A considerable portion of NMO-related spinal cord damage occurs after diminution of vision, and the interval may be days, weeks, months or even years, eventually leading to paraplegia, sensory and sphincter dysfunction, and possibly respiratory muscle paralysis in the worst case. Because recurrent NMO has many common characteristics with recurrent optic neuritis with regard to the early clinical manifestations, recurrent NMO is easy to be misdiagnosed as the latter. In this case, in one aspect, the treatment opportunity is delayed, and in another aspect, the treatment means for optic neuritis aggravates the condition of NMO, thereby causing more serious consequences.

For a long time, there has been controversy about whether NMO is an independent disease or a multiple sclerosis (MS) subtype, and studies in recent years find that the aquaporin 4 (AQP4) autoantibody (AQP4-Ab) in serum is a very specific index in NMO diagnosis, and shows relatively high sensitivity (68%-91%) and specificity (85%-99%) in NMO diagnosis.

NMO is special due to its special pathogenesis. Further studies have shown that AQP4-Ab specifically binds to AQP4 on the astrocyte end foot in the central nervous system (CNS). It is now known that the damaging effect of AQP4-Ab on astrocytes can be achieved by both complement-dependent cytotoxicity and antibody-dependent cytotoxicity. According to the latest report of Verkman research team, the injection of AQP4-Ab into brain parenchyma will cause NMO-like tissue lesions. Specific pathological changes include: damage of astrocytes, decrease of oligodendrocytes, myelin loss, and neuronal apoptosis. This phenomenon is partially similar to pathological changes occurring in patients and can therefore be used to study the pathogenic mechanism at the cellular level during the onset of NMO. The current relatively consistent view about the pathogenic mechanism of NMO is that AQP4-Ab causes death of astrocytes first and then causes demyelinating disease, during which a large number of inflammatory factors are released along with abnormal activation of microglial cells, so that an inflammatory pathogenic microenvironment for NMO disease is formed. The research focusing on AQP4 and the discovery of AQP4-Ab finally separate NMO from multiple sclerosis.

SUMMARY

Technical Problem

Current treatments for NMO mainly include treatment in the acute phase and treatment in the remission phase. The treatment in the acute phase is intended to reduce the dysfunction of the nervous system as much as possible and promote the recovery from disease, and at present, the treatment mainly includes high-dose methylprednisolone impact treatment, plasma exchange, intravenous injection of immunoglobulin and cyclophosphamide, and the like; the treatment in the remission phase is primarily intended to reduce the number and severity of relapses, and mainly includes use of immunosuppressive agents, including azathioprine, mycophenolate mofetil, mitoxantrone, methotrexate, rituximab, and the like. However, the existing treatment methods are all featuring extensive inhibition of the systemic immune system to relieve systemic autoimmune reaction, and they bring relatively large systemic side effect to patients, have the risk of causing serious infection, and are easy to cause hormone tolerance and thereby cause treatment failure.

Therefore, safe and effective drugs for NMO are in acute shortage, clinical needs are not met, and thus there is an urgent need to develop new drugs for treating the disease.

Solution to Problem

Technical Solution

In order to solve the above problem in the prior art, the present disclosure, through research, provides use of a sesquiterpene lactone compound for manufacturing a drug for treating optic neuritis.

According to another preferred embodiment of the present disclosure, the optic neuritis is neuromyelitis optica.

According to another preferred embodiment of the present disclosure, the sesquiterpene lactone compound and a pharmaceutically acceptable auxiliary material are formulated into a medicament.

According to another preferred embodiment of the present disclosure, the medicament is a liquid, gaseous, solid or semisolid formulation.

According to another preferred embodiment of the present disclosure, the medicament is an injection.

According to another preferred embodiment of the present disclosure, the medicament is an oral formulation.

According to another preferred embodiment of the present disclosure, the oral formulation is a capsule.

According to another preferred embodiment of the present disclosure, the oral formulation is a pill.

In another preferred embodiment of the present disclosure, the sesquiterpene lactone compound is a micheliolide derivative.

Beneficial Effects of Present Disclosure

Beneficial Effects

In the present disclosure, the sesquiterpene lactone compound is used for manufacturing a drug for treating optic neuritis for the first time, and the manufactured drug has a good curative effect on treating neuromyelitis optica.

BRIEF DESCRIPTION OF THE DRAWINGS

Description of Drawings

Figure 1:
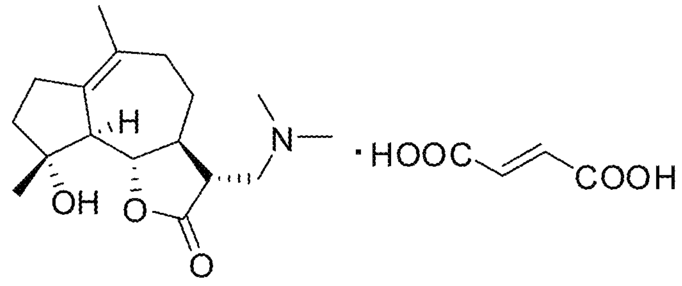
Figure 2:
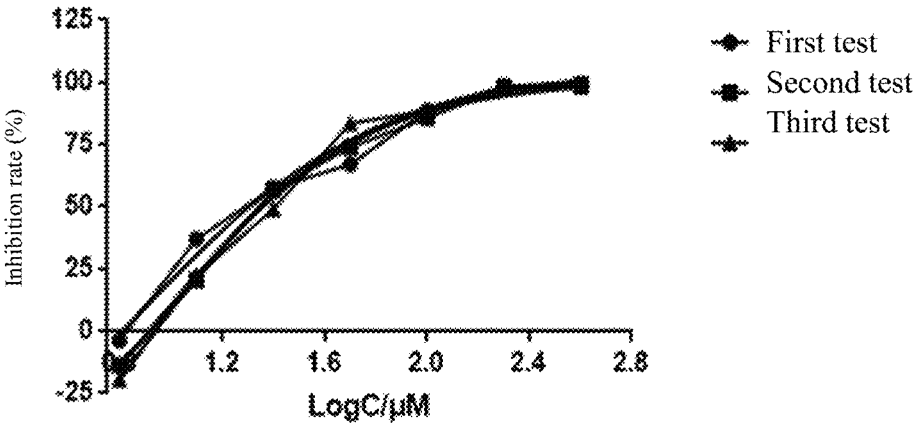
Figure 3:
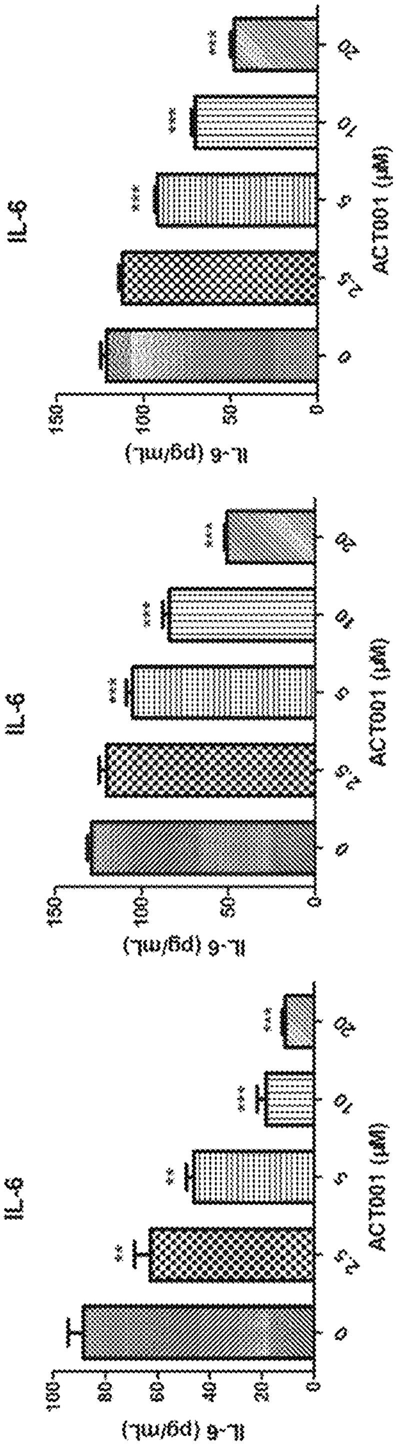
Figure 4:
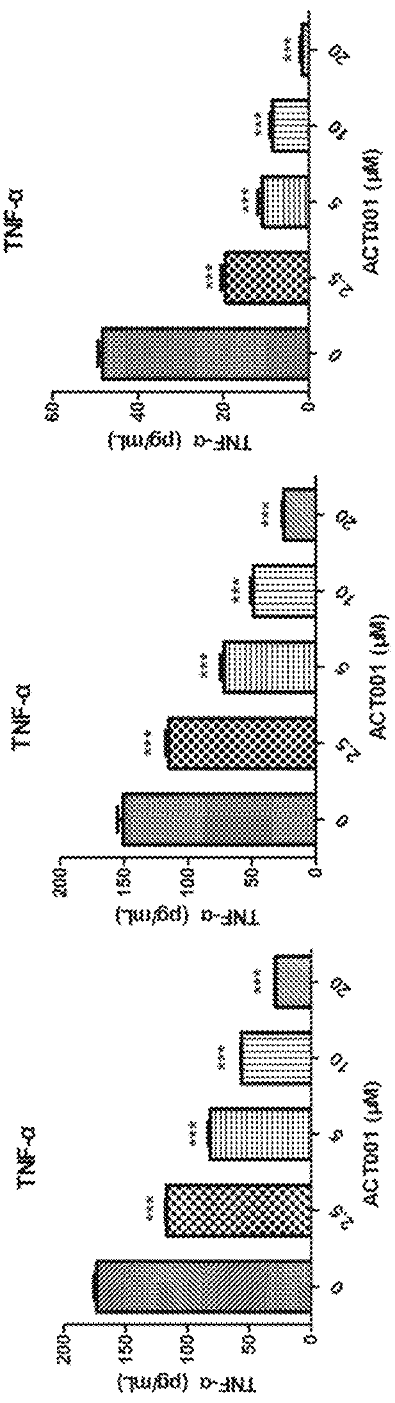
Figure 5:
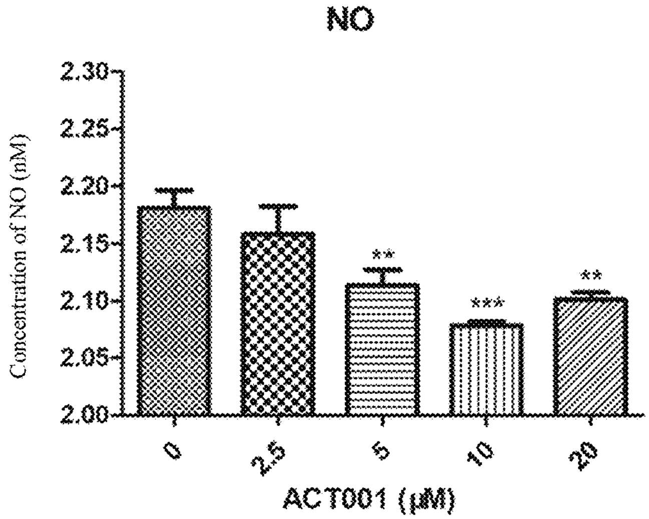
Figure 6:
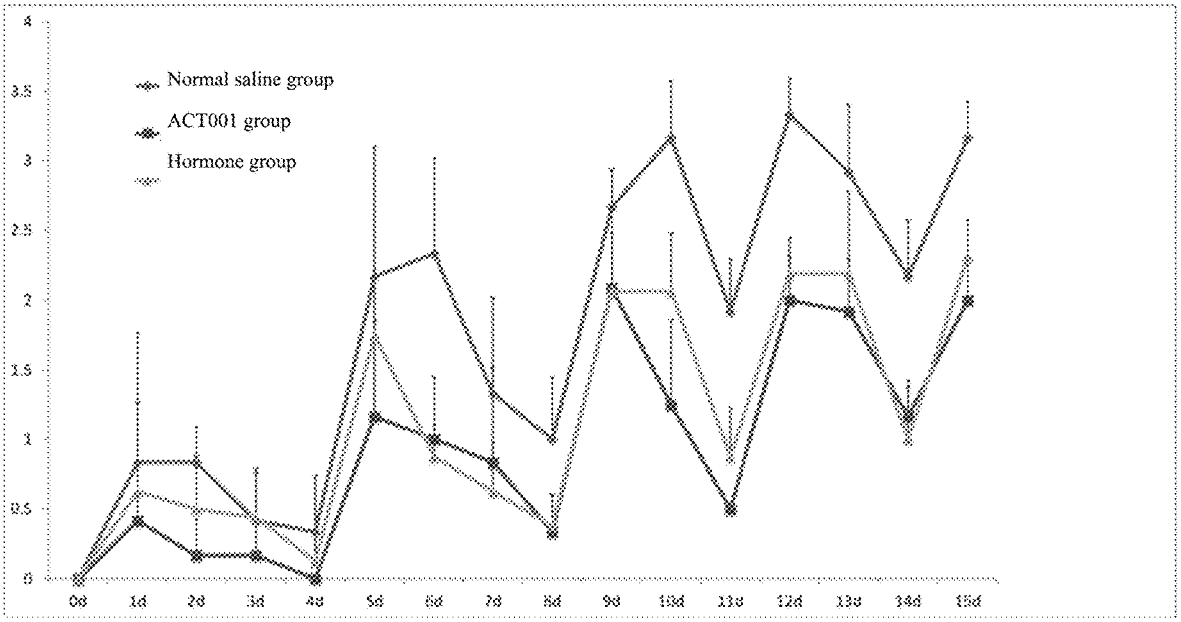

FIG. 1 is the molecular formula of ACT001 according to an example of the present disclosure;

FIG. 2 is a graph showing the results of a cytotoxicity experiment of ACT001 for BV-2 cells according to an example of the present disclosure;

FIG. 3 is a graph showing the inhibition of IL-6 release by ACT001 after LPS activation of BV-2 according to an example of the present disclosure;

FIG. 4 is a graph showing the inhibition of TNF-α release by ACT001 after LPS activation of BV-2 according to an example of the present disclosure;

FIG. 5 is a graph showing the inhibition of NO release by ACT001 after LPS activation of BV-2 according to an example of the present disclosure; and FIG. 6 is a graph showing the scores of ACT001 in relieving symptoms of Lewis rat NMO disease models according to an example of the present disclosure.

BEST EXAMPLE OF IMPLEMENTING THE PRESENT DISCLOSURE

Best Embodiment of the Present Disclosure

The present disclosure is described in detail below with reference to the drawings, and the description in this section is only exemplary and explanatory and should not be construed as limiting the scope of the present disclosure in any way. Furthermore, features of examples described in this document and various examples may be combined by those skilled in the art accordingly, based on the description in this document.

EXAMPLE 1

The sesquiterpene lactone compound used for manufacturing a drug for treating neuromyelitis optica studied in this example has a molecular formula shown in FIG. 1. It is also known as ACT001, which has a chemical name of (3R,3aS,9R,9aS,9bS)-3-((dimethylamino)methyl)-9-hydroxy-6,9-dimethyl-3,3a,4,5,7,8,9,9a-octahydroazuleno[4,5-b]furan-2(9bH)-one fumarate, and is a micheliolide derivative. The molecular formula is shown in FIG. 1. In this example, ACT001 is used to perform a therapeutic study on AQP4 autoimmune antibody positive neuromyelitis optica patients.

The pharmacological efficacy experiment is as follows:

1. We first performed in vitro experiments on the active ingredient. According to the results of the in vitro experiments, ACT001 could inhibit the proliferation of BV-2 cells with an $IC_{50}$ value of 23.6 μM, and could remarkably reduce the release of microglial inflammatory factors (TNF-α, IL-6, NO) activated by LPS at 10 μM and reduce of inflammatory response of microglial cells.

Meanwhile, before establishing NMO animal models, firstly, the spinal intrathecal catheterization was performed on Lewis rats, wherein an outlet could be placed at the spinal cord and at the first lumbar vertebra of the rat by controlling the length (7 cm) of a PE10 soft tube. For the Lewis rats after spinal intrathecal catheterization, they had no difference in behavior from normal rats the next day after the operation. Successfully modeled rats were divided into three groups, and 10 μL of each of the serum and complement system of an NMO patient was injected into the soft tubes in the rats for which the intubation was successful, and the supplementation was performed every four days. The administration regimen was as follows: the model control group (6 animals) was intragastrically administered normal saline every day for 15 consecutive days; the hormone group (8 animals) was intragastrically administered the methylprednisolone amber solution for injection every day at a dose of 30 mg/kg for 15 consecutive days; and the ACT001 group (6 animals) was intragastrically administered the ACT001 solution every day at a dose of 60 mg/kg for 15 consecutive days. The animal state was observed daily, and behavioral scores were recorded based on animal symptoms. The results showed that animals in the ACT001 group were well tolerated, and disease symptoms were significantly alleviated compared to the normal saline control group; and the ACT001 group showed a similar effect of alleviation and substantially equal overall score compared to the hormone treatment group.

We then intended to use ACT001 for treating neuromyelitis optica. ACT001 can effectively inhibit the inflammatory response of microglial cells, and can significantly reduce the release of inflammatory factors, including NO, TNF-α, and IL-6. We first evaluated the effect of ACT001 on the proliferation activity of the microglial cell BV2 by using the MTT method and the CCK8 method in vitro, and the results showed that ACT001 had the effect of inhibiting the proliferation of BV2 cells in vitro, which was specifically shown in that the $IC_{50}$ value of ACT001 for BV2 cells was 23.6±2.34 μM (see Table 1 and FIG. 2).

TABLE 1

In vitro activity inhibition of ACT001 against BV2 cells

| Cell line | $IC_{50}$(μM) | $IC_{90}$(μM) |
|---|---|---|
| BV2 | 23.6 ± 2.34 | 99.13 ± 10.25 |

2. In vitro activity inhibition of ACT001 against BV2 cells

BV2 cells were digested, counted and plated in a 24-well plate at 1 mL and 20,000 cells per well, and the cells were then incubated overnight in an incubator at 5% $CO_2$ and 37° C. 1 μg/mL LPS was added into each well for 1 h of action, and then ACT001 at different concentrations was added. Five experimental groups were set, namely: (1) control group; (2) ACT001-2.5 μM group; (3) ACT001-5 μM group; (4) ACT001-10 μM group; and (5) ACT001-20 μM group. After 8 h of action, the drug action was completed, the supernatant was collected and centrifuged at 12,000 rpm for 20 min, and then ELISA was performed according to the kit instructions.

FIG. 2 is a graph showing the effect of ACT001 on the proliferation activity of BV2 cells. It can be seen from FIG. 2 that: all the ACT001 groups could reduce IL-6 expression in BV-2 cells compared to the control group, and the inhibition was enhanced with the increase in the ACT001 dose, showing a dose-dependent trend; and the p values of ACT001 10 μM and 20 μM dose groups were both less than 0.001, i.e. significantly reduced, compared to the control group, and the repeat trends were consistent in three tests.

3. Effect of ACT001 on IL-6 expression

BV2 cells were digested, counted and plated in a 24-well plate at 1 mL and 40,000 cells per well, and the cells were then incubated overnight in an incubator at 5% $CO_2$ and 37° C. 1 μg/mL LPS was added into each well for 1 h of action, and then ACT001 at different concentrations was added. Five experimental groups were set, namely: (1) control group; (2) ACT001-2.5 μM group; (3) ACT001-5 μM group; (4) ACT001-10 μM group; and (5) ACT001-20 μM group. After 24 h of action, the drug action was completed, the supernatant was collected and centrifuged at 12,000 rpm for 20 min, and then ELISA was performed according to the kit instructions.

FIG. 3 shows the effect of ACT001 on IL-6 expression (*$P<0.05$, $P<0.01$, *$P<0.001$). It can be seen from FIG. 3 that: all the ACT001 groups could reduce TNF-α expression in BV-2 cells compared to the control group, and the inhibition was enhanced with the increase in the ACT001 dose, showing a dose-dependent trend; and the p values of ACT001 dose groups were all less than 0.001, i.e. significantly reduced, compared to the control group, and the repeat trends were consistent in three tests.

4. Effect of ACT001 on TNF-α expression

BV2 cells were digested, counted and plated in a 24-well plate at 1 mL and 40,000 cells per well, and the cells were then incubated overnight in an incubator at 5% $CO_2$ and 37°

C. 1 μg/mL LPS was added into each well for 1 h of action, and then ACT001 at different concentrations was added. Five experimental groups were set, namely: (1) control group; (2) ACT001-2.5 μM group; (3) ACT001-5 μM group; (4) ACT001-10 μM group; and (5) ACT001-20 μM group. After 24 h of action, the drug action was completed, the supernatant was collected and centrifuged at 12,000 rpm for 20 min, and then ELISA was performed according to the kit instructions.

FIG. 4 shows the effect of ACT001 on TNF-α expression (*P<0.05,  P<0.01, * P<0.001). It can be seen from FIG. 4 that the ACT001 2.5 μM, 5 μM and 10 μM dose groups all could reduce TNF-α expression in BV-2 cells compared to the control group, and the inhibition was enhanced with the increase in the ACT001 dose, showing a dose-dependent trend, wherein the expression in the ACT001 10 UM dose group was significantly reduced compared to that in the control group.

5. FIG. 5 is a graph showing the effect of ACT001 on NO expression (*P<0.05,  P<0.01, * P<0.001). It can be seen from FIG. 5 that ACT001 significantly could reduce the pathological release of microglial cells NO at a concentration of only 5 μM.

6. Effect of ACT001 on NMO patient in vitro tests and animal models

10 μL of each of the serum and complement system of an NMO patient was injected into the soft tubes in the rats for which the spinal intrathecal catheterization was successful, and the supplementation was performed every four days, thus establishing the NMO animal models. Model animals were randomized into three groups, namely: the normal saline group, the hormone (methylprednisolone sodium succinate for injection) group and the ACT001 group, and the administration regimen is as follows:

| Group | Number of animals | Therapeutic drug | Dose | Route of administration and course of treatment |
|---|---|---|---|---|
| A | 6 | Normal saline | | Intragastric administration*15 times |
| B | 8 | Methylprednisolone sodium succinate for injection | 30 mg/kg | Intragastric administration*15 times |
| C | 6 | ACT001 | 60 mg/kg | Intragastric administration*15 times |

That is, the dose of group B was equivalent to about 5 mg/kg of ACT001 administered to a human after ACT001 and a pharmaceutically acceptable auxiliary material were formulated into a medicament, and the dose of group C was equivalent to about 10 mg/kg of ACT001 administered to a human after ACT001 and a pharmaceutically acceptable auxiliary material were formulated into a medicament.

Behavioral scoring was performed based on animal symptoms.

The scoring criteria were as follows:

0 point: no clinical symptoms;

1 point: decreased tail tension or mild gait clumsiness;

2 points: no tail tension or moderate gait abnormality; weakness of both hind limbs and recovery after being turned over passively;

3 points: paralysis of both hind limbs. no recovery after being turned over passively, but capable of moving after stimulation;

4 points: paralysis of both hind limbs. paralysis or weakened muscle strength of the forelimbs with urinary and fecal incontinence;

5 points: moribund state or dead.

Symptoms between two stages were measured as ±0.5.

The results of the experiment showed that during administration, animals in the ACT001 group were well tolerated, and disease symptoms were significantly alleviated compared to the normal saline control group; and the ACT001 group showed a similar effect of alleviation and substantially equal behavioral score compared to the hormone treatment group. The results of the experiment are shown in Table 2 and FIG. 6:

TABLE 2

| Behavioral scores of animals in each group | | | | | | | | |
|---|---|---|---|---|---|---|---|---|
| | Days of treatment (days) | | | | | | | |
| | 0 | 1 | 2 | 3 | 4 | 5 | 6 | 7 |
| Normal saline group | 0.00 ± 0.00 | 0.83 ± 0.93 | 0.83 ± 0.26 | 0.42 ± 0.38 | 0.33 ± 0.41 | 2.17 ± 0.93 | 2.33 ± 0.68 | 1.33 ± 0.68 |

TABLE 2-continued

| Behavioral scores of animals in each group | | | | | | | | |
|---|---|---|---|---|---|---|---|---|
| ACT001 group | 0.00 ± 0.00 | 0.42 ± 0.20 | 0.17 ± 0.26*** | 0.17 ± 0.26 | 0.00 ± 0.00 | 1.17 ± 0.68 | 1.00 ± 0.45** | 0.83 ± 0.68 |
| Hormone group | 0.00 ± 0.00 | 0.63 ± 0.64 | 0.50 ± 0.38 | 0.44 ± 0.32 | 0.13 ± 0.23 | 1.75 ± 0.46 | 0.88 ± 0.23*** | 0.63 ± 0.35 |
| | Days of treatment (days) | | | | | | | |
| | 8 | 9 | 10 | 11 | 12 | 13 | 14 | 15 |
| Normal saline group | 0.00 ± 0.45 | 2.67 ± 0.26 | 3.17 ± 0.41 | 1.92 ± 0.38 | 3.33 ± 0.26 | 2.92 ± 0.49 | 2.17 ± 0.41 | 3.17 ± 0.26 |
| ACT001 group | 0.33 ± 0.26* | 2.08 ± 0.86 | 1.25 ± 0.61*** | 0.50 ± 0.00*** | 2.00 ± 0.32*** | 1.92 ± 0.38** | 1.17 ± 0.26*** | 2.00 ± 0.32*** |
| Hormone group | 0.38 ± 0.23* | 2.06 ± 0.42* | 2.06 ± 0.42*** | 0.88 ± 0.35*** | 2.19 ± 0.26*** | 2.19 ± 0.59* | 1.00 ± 0.38*** | 2.31 ± 0.26*** |

Note:
as compared to normal saline,
*P < 0.05,
**P < 0.01,
***P < 0.001

FIG. 6 shows behavioral scores of animal models. It can be seen from Table 2 and FIG. 6 that ACT001 could significantly reduce the behavioral scores of NMO animal models and alleviate symptoms of NMO disease models, and its action effect was not weaker than that of hormone.

Table 3 shows in vivo pharmacodynamic test.

TABLE 3

| Research project | Test system and strain | Route and frequency of administration | Major research results |
|---|---|---|---|
| Research on effectiveness of ACT001 in relieving symptoms of neuromyelitis optica. | 20 Lewis rats, ♀. | The negative control group was orally and intragastrically administered normal saline. The ACT001 group was intragastrically administered once daily for 15 times. The methylprednisolone sodium succinate group was intragastrically administered once daily for 15 times. | The behavioral score of the negative control group was 3.2 ± 0.3; The behavioral score of the ACT001 group was 2.0 ± 0.3; The behavioral score of the methylprednisolone sodium succinate group was 2.0 ± 0.3. |

In vivo pharmacodynamic test

As can be seen from the above results, ACT001 has a significant advantage in the treatment of NMO. By performing the ACT001 in vitro activity test, it was found that the $IC_{50}$ value of the ACT001 for microglial cell BV-2 was 23.6 μM, and the release of inflammatory factors including NO, TNF-α and IL-6 could be significantly reduced, so that the microglial inflammatory response triggered by LPS stimulation was inhibited.

In the neuromyelitis optica animal models, experimental results showed that ACT001 could significantly relieve clinical symptoms of the neuromyelitis optica animal models, and after consecutive administration for 15 days, the behavioral score of the normal saline group was 3.17±0.26, while that of the ACT001 group was 2.00±0.32, which was basically equivalent to 2.31±0.26 of the hormone group. This indicates that ACT001 can replace hormone to become a new treatment mode for NMO diseases clinically.

ACT001 was our first choice. In addition to ACT001, derivatives of micheliolide and salts thereof also have therapeutic effect on neuromyelitis optica, according to the experiments described above.

The example described above is a preferred embodiment of the present disclosure, which, however, is not intended to limit the embodiments of the present disclosure. Any other changes, modifications, substitutions, combinations, and simplifications can be made without departing from the spirit and principle of the present disclosure, and should be the equivalent replacements and included in the protection scope of the present disclosure.

The invention claimed is:

1. A method for the treatment of neuromyelitis optica, comprising administering to a person in need thereof an effective amount of a sesquiterpene lactone compound having the following structural formula:

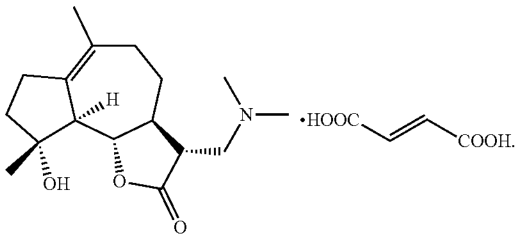

2. The method according to claim 1, wherein the neuromyelitis optica is AQP4 autoimmune antibody positive neuromyelitis optica.

3. The method according to claim 1, wherein the sesquiterpene lactone compound is administered in a medicament that is in a liquid, gaseous, solid, or semi-solid formulation.

4. The method according to claim 3, wherein the medicament is an injection.

5. The method according to claim 3, wherein the medicament is an oral formulation.

* * * * *